(12) United States Patent
Pavlovich et al.

(10) Patent No.: US 7,970,096 B2
(45) Date of Patent: Jun. 28, 2011

(54) METHOD OF AND SYSTEM FOR LOW COST IMPLEMENTATION OF DUAL ENERGY CT IMAGING

(75) Inventors: Julia Pavlovich, Cambridge, MA (US);
Aleksander Roshi, Medford, MA (US);
Ram Naidu, Newton, MA (US); Sergey Simanovsky, Brookline, MA (US);
Zhengrong Ying, Belmont, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 12/349,893

(22) Filed: Jan. 7, 2009

(65) Prior Publication Data
US 2010/0172464 A1 Jul. 8, 2010

(51) Int. Cl.
*A61B 6/03* (2006.01)
*H05G 1/64* (2006.01)
*G21K 3/00* (2006.01)
(52) U.S. Cl. .............. 378/5; 378/19; 378/98.9; 378/156; 378/158
(58) Field of Classification Search ................ 378/5, 19, 378/57, 98.9, 98.11, 156, 157, 158, 159
See application file for complete search history.

(56) References Cited

U.S. PATENT DOCUMENTS

| | | | | |
|---|---|---|---|---|
| 3,521,058 | A * | 7/1970 | Mittelstaedt | 378/156 |
| 5,400,379 | A * | 3/1995 | Pfoh et al. | 378/19 |
| 5,640,436 | A * | 6/1997 | Kawai et al. | 378/4 |
| 5,661,774 | A | 8/1997 | Gordon et al. | |
| 5,802,134 | A * | 9/1998 | Larson et al. | 378/4 |
| 5,966,422 | A * | 10/1999 | Dafni et al. | 378/9 |
| 6,292,538 | B1 * | 9/2001 | Hell et al. | 378/137 |
| 6,332,015 | B1 * | 12/2001 | Honda | 378/98.11 |
| 6,611,578 | B2 * | 8/2003 | Snoeren et al. | 378/158 |
| 6,650,730 | B2 * | 11/2003 | Bogatu et al. | 378/158 |
| 7,426,260 | B2 * | 9/2008 | Cantu et al. | 378/98.8 |
| 7,649,981 | B2 * | 1/2010 | Seppi et al. | 378/158 |
| 2005/0012046 | A1 * | 1/2005 | Groh et al. | 250/370.09 |
| 2008/0247504 | A1 * | 10/2008 | Edic et al. | 378/9 |
| 2009/0147910 | A1 * | 6/2009 | Edic et al. | 378/5 |

OTHER PUBLICATIONS

Flohr, et al., First performance evaluation of a dual-source CT (DSCT) system, Eur Radiol (2006) 16:256-268.

* cited by examiner

*Primary Examiner* — Allen C. Ho
(74) *Attorney, Agent, or Firm* — McDermott Will & Emery, LLP

(57) ABSTRACT

The disclosed CT scanner comprises at least one source of X-rays; a detector array comprising a plurality of detectors; and an X-ray filter mask arrangement disposed between the source of X-rays and detector array so as to modify the spectra of the X-rays transmitted from the source through the mask to at least some of the detectors so that the X-ray spectra detected by at least one set of detectors is different from the X-ray spectra detected by at least one other set of detectors.

12 Claims, 5 Drawing Sheets

METHOD OF AND SYSTEM FOR LOW COST IMPLEMENTATION OF DUAL ENERGY CT IMAGING

FIELD

The present application relates generally to CT scanners, and more particularly to a CT scanner including a detector array in which the number of spectral energy levels to which the detector array is responsive is increased in a relatively low cost and simple manner so that, for example, a single energy scanner can easily be converted to operate as a dual energy scanner.

BACKGROUND

Airport scanners are one of the main tools in deterring and preventing contraband, such as explosives, guns and knives, and other prohibited items, from being brought on board an airplane. Current scanners include line scanners where bags are transported between a detector array and one or more X-ray sources. These scanners can miss the detection of contraband if the contraband is of a certain shape, and the bag containing the contraband is oriented in a certain direction. Such scanners rely heavily on the operator's alertness to possible threats. CT scanners are much better at scanning bags because they can produce views through a bag in many different directions, and can incorporate automatic threat detection. Additionally, dual energy CT scanners have been developed to reduce the false alarm rate associated with the automatic threat detection by providing atomic number measurements of scanned objects in addition to density measurements. Different dual energy implementation schemes have been proposed or developed. One dual energy implementation scheme is to use a switching high voltage power supply. See for example, Bernard M. Gordon, et al., "Dual energy power supply," U.S. Pat. No. 5,661,774, assigned to the present assignee. Recently one CT manufacturer has developed a dual-source CT scanner, which uses two x-ray tubes placed within one single gantry and is capable of dual energy imaging. See, for example, T. G. Flohr, et al., "First performance evaluation of a dual-source CT (DSCT) system," European Radiology 16 (2), 256-268 (2006). The widely used passive "sandwich" detectors, e.g. the detectors used in the system described in H. Takeo, et al., "A new FCR image processing function: energy subtraction FCR9501 ES/FCR DX-A," Fuji Comput. Radiogr. Tech. Rev. 4, 1-24, 1995., provide dual energy imaging capability with a single X-ray source. All these implementations require special designs and are usually very costly. In addition, these implementation schemes are not suitable for easily upgrading existing single energy CT scanners, particularly of interest to security applications, to obtain dual energy imaging capability for reducing the false alarms from the automatic threat detection system. Efforts are constantly directed towards finding ways to decrease the costs of CT security scanners while maintaining many of the advantages of dual energy CT scanning systems, and to develop a simple and easy way to convert current single energy scanners into dual energy scanners.

SUMMARY

In accordance with one aspect of the present disclosure, a low cost implementation scheme of dual energy imaging is provided. The low cost implementation scheme uses a filter mask with a pattern of two or more sections, such as a checker board layout, placed on top of a two-dimensional detector array. In such a layout, the detectors covered by the filter mask become the high-energy detectors because of the spectral filtering by the filter mask, and the detectors that are not covered or thinly covered by the filter mask become the low-energy detectors. Such a dual energy implementation scheme does not require a design change of the existing beam-line of a single energy CT scanner to be upgraded into a dual energy CT scanner.

In accordance with another aspect of the present disclosure, the material and the thickness of the filter mask are chosen to maximize the x-ray spectral separation between the high-energy and low-energy spectra while a) maintaining the dynamic ranges of the X-ray photons within the limits of the detectors and corresponding electronics; and b) offering enough penetration for objects to be scanned. The spectral separation can be defined by a weighted sum of the high-energy and low-energy projection differences of a collection of objects of interest, and can be simulated using scanner geometry, x-ray source, and detector properties to perform the optimization over materials and thicknesses of a material.

In accordance with still another aspect of the disclosure, any one of several interpolation schemes can be used to generate both high-energy and low-energy projection data of the complete detector array. For example, a two-dimensional linear interpolation can be used. This two-dimensional linear interpolation can be incorporated into the reconstruction algorithm, for example, during cone-beam to fan-beam conversion in NSR (Nutating Slice Reconstruction) interpolation. Additionally, a flying focal spot can be used to compensate for the reduction of the image resolution caused by interpolation.

GENERAL DESCRIPTION OF THE DRAWINGS

DETAILED DESCRIPTION OF THE DRAWINGS

Figure 1:
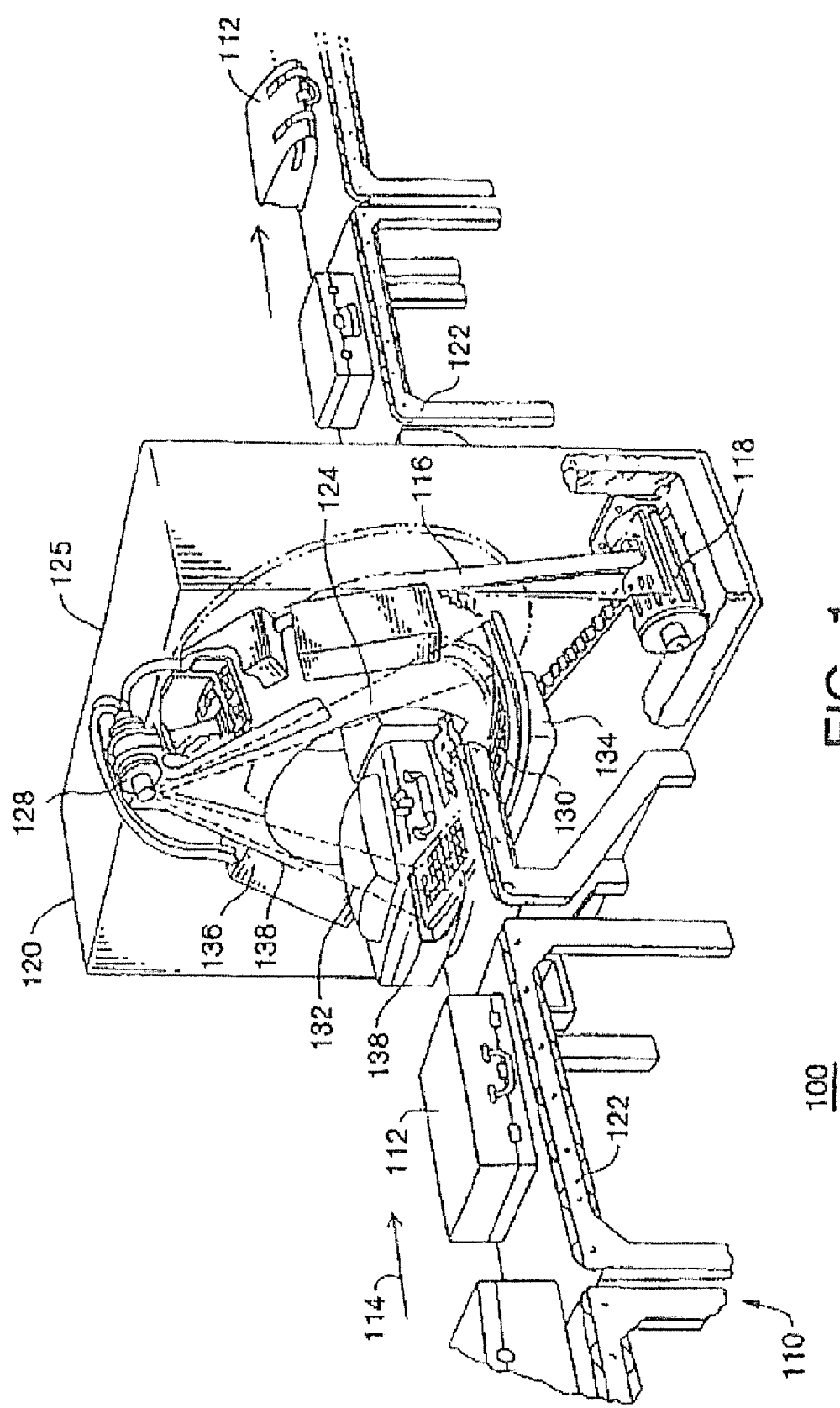
FIG. 1 is a perspective view of a baggage scanning system including the X-ray source designed to provide at least two which can be adapted to incorporate the system and perform method described herein.
Figure 2:
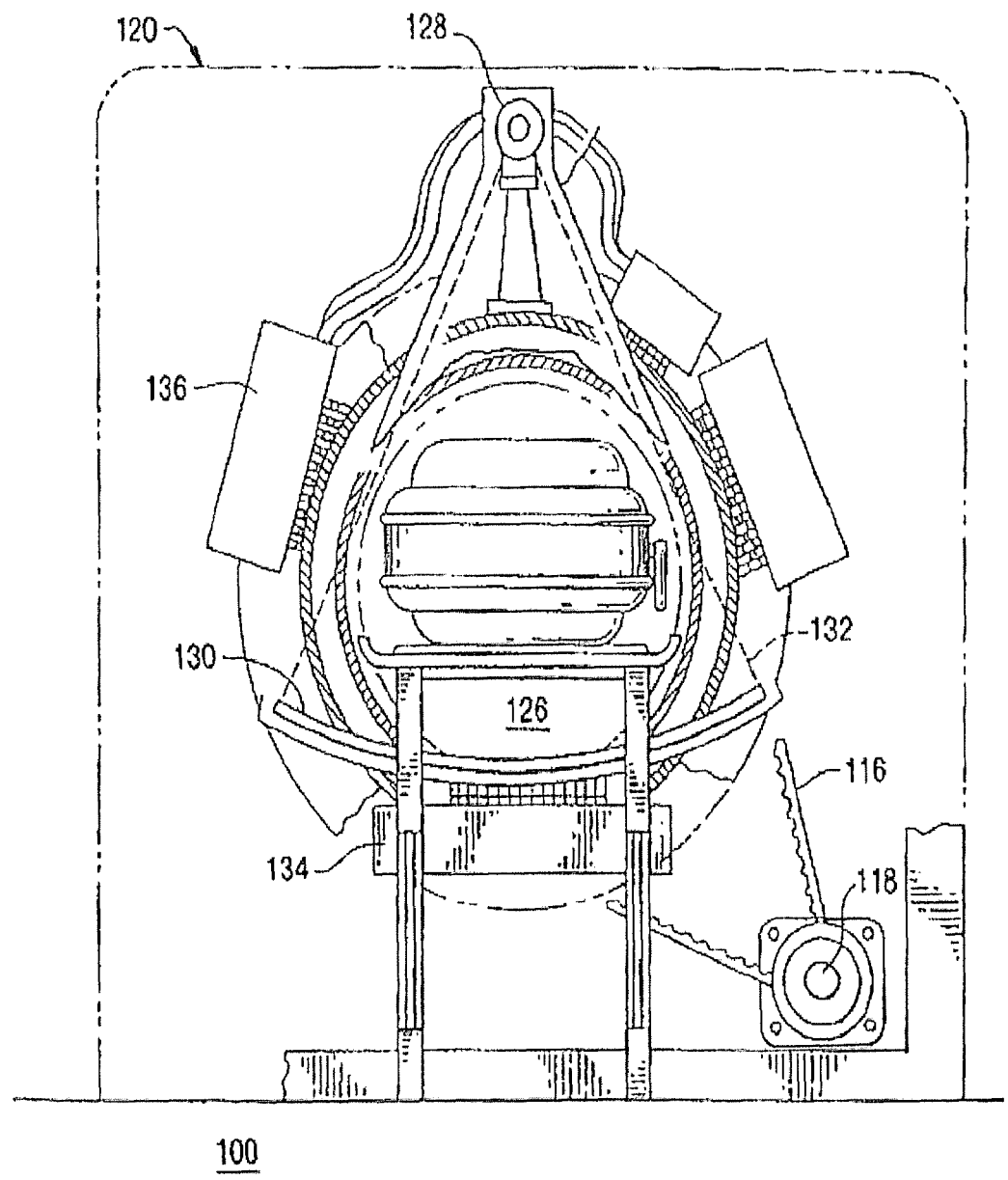
FIG. 2 is a cross-sectional end view of the system of FIG. 1.
Figure 3:
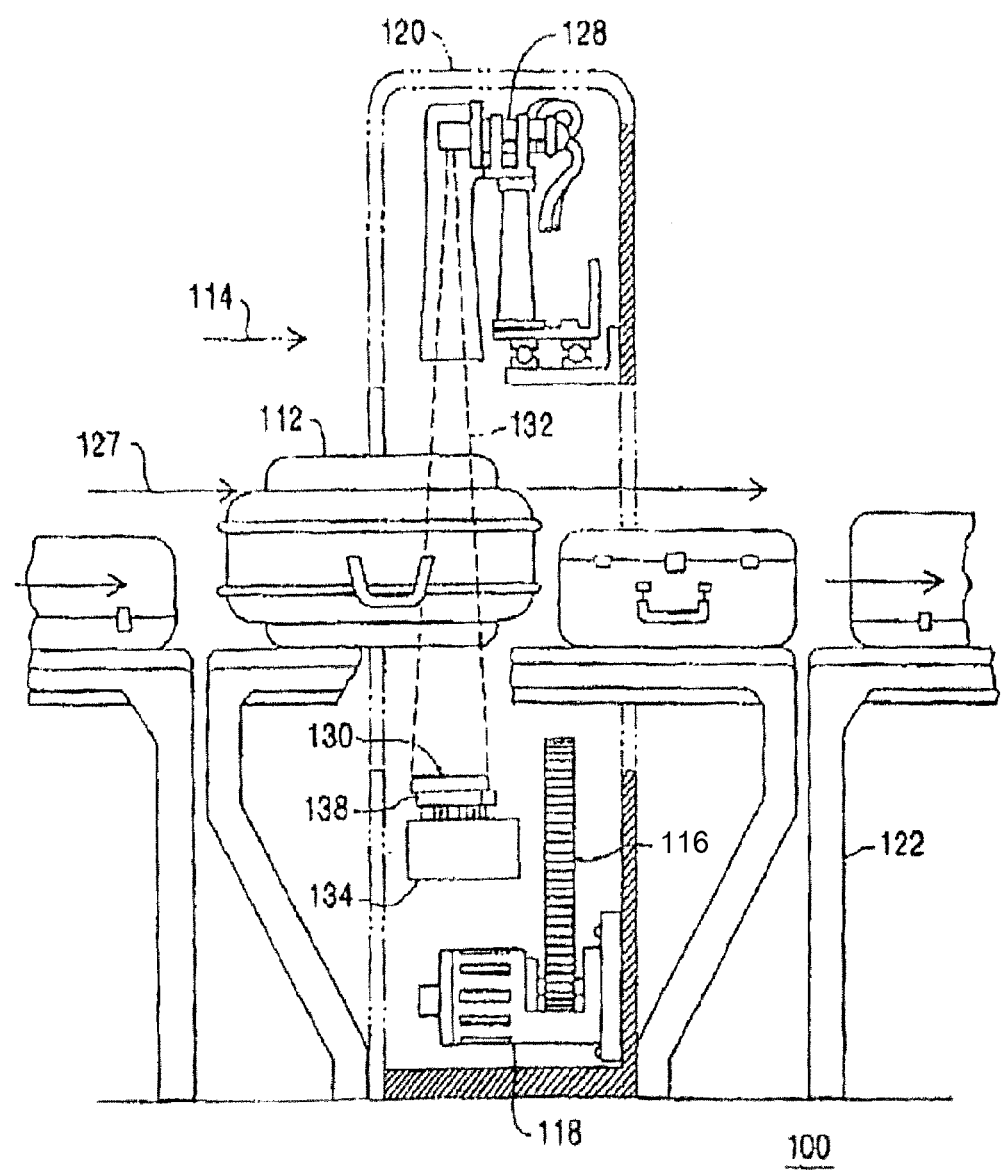
FIG. 3 is a cross-sectional radial view of the system of FIG. 1.

Referring to the drawings, FIGS. 1, 2 and 3 show perspective, end cross-sectional and radial cross-sectional views, respectively, of one embodiment of a baggage scanning system 100. The baggage scanning system 100 includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism. Rotating platform 124 defines a central aperture 126 through which conveyor system 110 transports the baggage 112. The rotation axis defines the Z-axis of the scanning system, while the X and Y-axes (perpendicular to the Z-axis) are disposed in the center scanning plane (normal to the Z-axis).

The system 120 includes an X-ray tube 128 and a detector array 130 which are disposed on diametrically opposite sides of the platform 124. The detector array 130 is preferably a two-dimensional array. The system 120 further includes a data acquisition system (DAS) 134 for receiving and processing signals generated by detector array 130, and an X-ray tube control system 136 for supplying power to, and otherwise controlling the operation of X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 includes at least one cathode and one anode for creating at least one separate focal spot from which an X-ray beam can be created and generated. The beam shown generally at 132 in FIGS. 1-3, passes through a three dimensional imaging field, through which conveying system 110 transports baggage 112. After passing through the baggage disposed in the imaging field, detector array 130 can receive each beam 132. The detector array then generates signals representative of the densities of exposed portions of baggage 112. The beams 132 therefore define a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. The data acquisition system 134 includes a processor subsystem for carrying out the data processing described herein.

Figure 4:
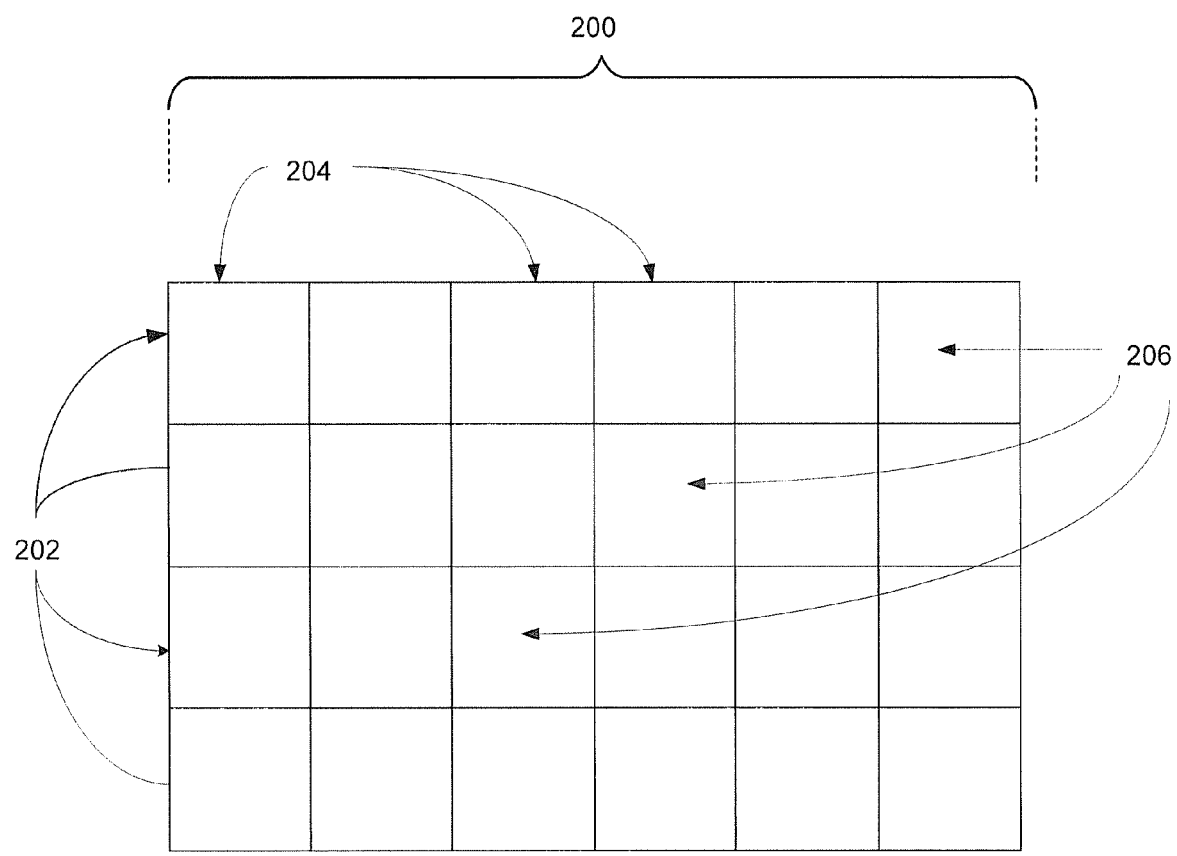
FIG. 4 is a simplified frontal view of some of the detectors of the detector array of the CT scanner.

FIG. 4 shows a portion of a typical two dimensional detector array 200, defined by individual rows 202 and columns 204 of detectors 206. Assume for purposes of illustration that the scanner includes a single energy source of X-rays, and that the scanner is capable of providing full volume 3-D CT images of all of the contents of a bag for multiple slices per rotation at small slice spacing. As mentioned above, dual energy CT scanners have been developed to reduce the false alarm rate of the automatic threat detection by providing atomic number measurements of scanned objects in addition to density measurements, but the costs associated with implementing dual energy in any one of the manners described above is relatively expensive. Again, each of the above-referenced implementations requires a special design. In addition, these implementation schemes are not suitable for upgrading existing single energy CT scanners, particularly of interest to security applications, to obtain dual energy imaging capability in order to reduce the false alarm rate from the automatic threat detection system.

Figure 5:
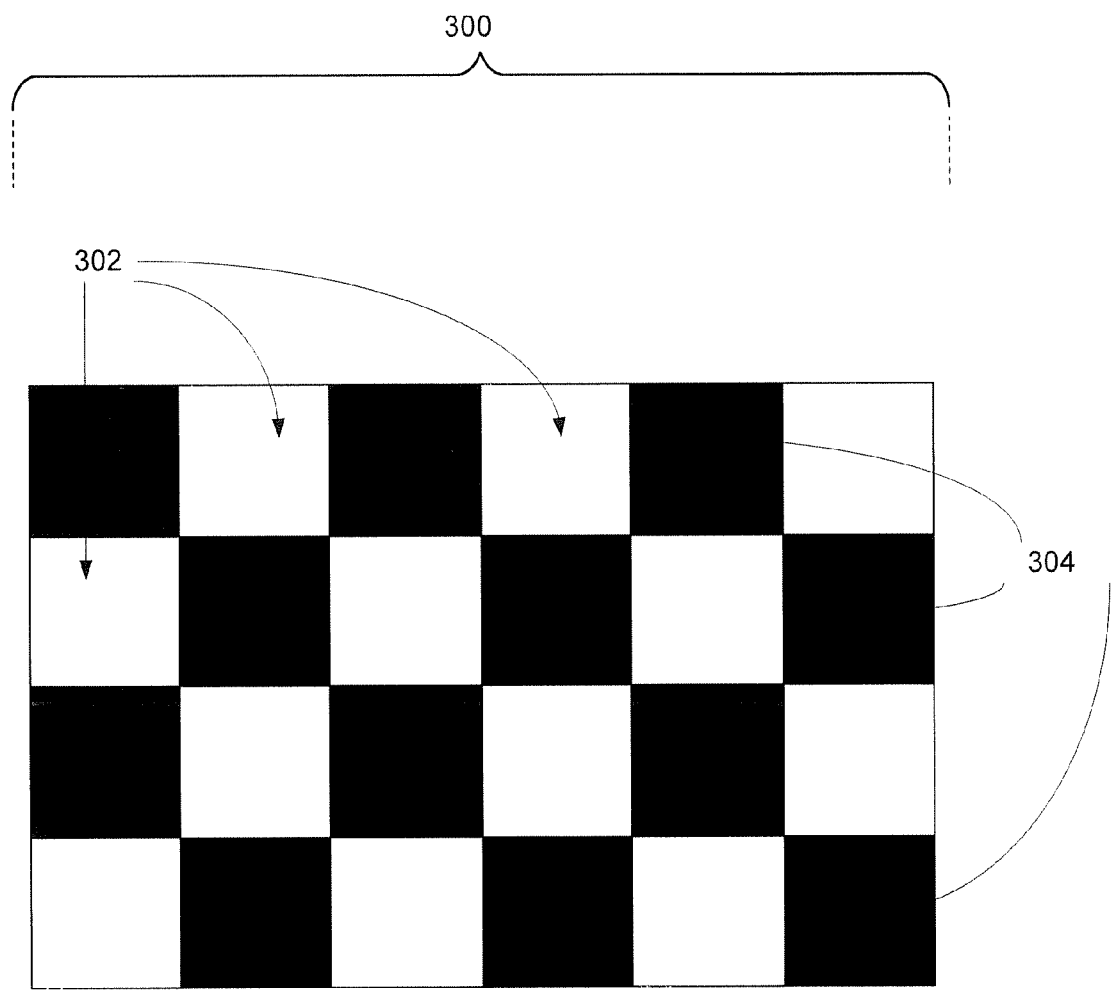
FIG. 5 is a simplified frontal view of a portion of the filter mask for using in the CT scanner for modifying the spectral portions of the X-ray beam penetrating the filter mask.

The disclosure describes an approach that can convert an existing single energy scanner to a dual energy scanner, simply and inexpensively so as to provide advantages of dual energy CT scanning systems. The approach includes the use of a filter mask shown in FIG. 5 in which the filter is provided with a pattern to match that of the array, so that when the mask is properly positioned in the path of the X-ray beam generated by the X-ray source between the source and the detector array, X-rays directed toward each detector will be passed through a filter section of one of at least two sets of filter sections indicated in FIG. 5 at 302 and 304, each having different X-ray transmission characteristics. In one embodiment the sections 302 are open spaces so that the X-rays pass directly through, in a second embodiment the sections 302 are made of a solid material to give rigidity to the mask but that is substantially transparent to X-rays, while in a third embodiment the sections 302 provide the second set of X-ray transmission characteristics so that the two types of sections 302 and 304 provide the dual energy characteristics. As shown, the pattern provided by the sections 302 and 304 provide a checkerboard pattern, although the specific pattern can vary. Further, although two different types of filter sections are shown in the drawing, a pattern can be provided with more than two so as to provide more than two different energy spectra to select areas of the detector array. The material and the thickness of the filter mask are chosen to maximize the X-ray spectral separation between the high-energy and low-energy spectra while a) maintaining the dynamic ranges of the X-ray photons within the limits of the detectors and corresponding electronics; and b) offering enough penetration for objects to be scanned. The spectral separation can be defined by a weighted sum of the high-energy and low-energy projection differences of a collection of objects of interest, and can be simulated using scanner geometry, X-ray source, and detector properties to perform the optimization over materials and thicknesses of a material. In a layout such as shown in FIG. 5, the detectors covered by the filter mask sections 304 become the high-energy detectors because of the spectral filtering by the filter mask, and the detectors aligned with sections 302 which provide little or no change to the energy spectra become the low-energy detectors. Alternatively, the sections 302 can be designed to provide a change to the energy spectra necessary to become the low energy spectra for the detectors below these sections. Further, in one embodiment a time multiplexing scheme can be used so that data can be alternately acquired and processed from signals acquired from the detectors receiving X-rays through sections 302 and signals acquired from the detectors receiving X-rays through sections 304. This allows the signals received from detectors receiving X-rays through sections 302 to be alternately processed with signals received from detectors receiving X-rays through sections 304, resulting in the number of processing channels being reduced by 50%, since data signals acquired from X-rays passing through each section 302 can share a channel with data acquired from X-rays passing through a corresponding section 304. Eliminating data from half the detectors for each reading necessitates however, that the missing data be replaced by interpolation techniques, some of which are described hereinafter.

The use of the mask 300 provides at least the following four potential advantages. The first benefit is a possible reduction of cost due to elimination of half of the DAS channels relative to the use of passive sandwich detectors. Second, demonstrated effects of bilinear interpolation indicate that the allowed number of adjacent bad detectors can be relaxed for the number of non-adjacent bad detectors. This advantage increases the production yield as well as lower the cost of the crystals used as a part of the detectors. Third, as mentioned above, a checker board detector array layout can be used for a mask that would change the spectral response of half of the detectors to produce dual energy measurements. The fourth benefit is a reduction by a factor of two of the required bandwidth for transmission of raw data from a gantry to a reconstruction computer. This advantage is due to transmission of half of the data after a removal of half of the channels.

After the elimination of half of the detector DAS channels, the missing detector samples are replaced, for example, by anyone of several interpolation techniques during image reconstruction. Thus, when a projection is made using the high energy spectra, only data acquired through detection of X-rays by the detectors disposed below sections 304 of the filter mask 300 are processed, while data associated with the other detectors are determined through interpolation. Similarly, when a projection is made using the low energy spectra, only data acquired through the detection of X-rays by the detectors disposed below sections 302 of the filter mask 300 are processed, while the data associated with the other detectors are determined through interpolation. Examples of four interpolation schemes are described below. The four schemes respectively use linear interpolation along the X-axis, linear interpolation along the Z-axis, four point Lagrange interpolation along the X-axis, and bilinear interpolation along the X and Z-axes. The reconstruction process is thus modified so as to include the interpolation procedure of the missing detector samples. The interpolation step is performed after the correction steps and before applying the Nutated Slice Reconstruction (NSR) algorithm.

In one embodiment, the scanner collects helical cone-beam projection data from a tilted detector array and reconstructs images using the Nutated Slice Reconstruction (NSR) algorithm. The NSR algorithm interpolates the cone-beam data along the Z-axis of the scanner to generate fan beam projections that lie approximately on a tilted plane. The fan beam projections are rebinned to obtain parallel projections using radial and tangential interpolations. The parallel projections are filtered and then backprojected into tilted slices. The tilted slices are interpolated along the Z-axis to produce axial slices for threat detection and visualization. The reconstruction process can also include steps to compensate for the interaction of X-rays with the object and the imperfections of the system. In particular, several corrections such as air, offset, bad detector corrections, can be done before applying the NSR reconstruction algorithm.

In the embodiment described, the reconstruction process is modified to further include an interpolation procedure for providing interpolated data for the missing detector samples from each view. In one implementation, the interpolation step is performed after the correction steps, and before applying the NSR reconstruction algorithm.

Four interpolation schemes are described, although others may be employed. The four include linear interpolation along the X-axis, linear interpolation along the Z-axis, four point Lagrange interpolation along the X-axis, and bilinear interpolation along the X and Z-axes.

In the following mathematical description, let $P[v, s, r]$ be the input bag data and $P_Z[v, s, r]$ be the output bag data after interpolation, where $v$ is the view index ($0 \leq v \leq N_V$), $s$ is the sample index ($0 \leq s \leq N_{det}$), and $r$ is the row index ($0 \leq r \leq N_{row}$). Bag data $P[v, s, r]$ includes $N_V$ views and $N_{det} \times N_{row}$ samples per view. The detector array comprises $N_{row} \times N_{det}$ detectors where the missing detectors (not used for the view) have the row and the column indices of the same parity.

In the case of linear Z-interpolation, the missing detector samples are interpolated from neighboring samples in the same column using linear interpolation. In particular, the removed detector samples are calculated as follows:

$$P_Z[v, s, r] = \begin{cases} w_l P[v, s, r-1] + w_r P[v, s, r+1], & s+r \text{ is even} \\ P[v, s, 1], & r = 0 \text{ and } s \text{ is even} \\ P[v, s, N_{row}-2], & r = N_{row}-1 \text{ and } s \text{ is odd} \\ P[v, s, r], & \text{otherwise} \end{cases} \quad (1)$$

wherein the weights are wl=wr=0.5. The detectors s in adjacent rows are equidistant by design. The missing sample at the boundary is replaced by the neighboring detector value in the adjacent row.

In the case of bilinear z and x interpolation, the removed detector samples are interpolated from the four nearest neighboring samples using bilinear interpolation. In particular, the removed detector samples are computed as follows:

$$P_{XZ}[v, s, r] = \begin{cases} w_z P[v, s, r-1] + w_z P[v, s, r+1] + \\ w_l P[v, s-1, r] + w_r P[v, s+1, r], & s+r \text{ is even} \\ P[v, s, r], & \text{otherwise} \end{cases} \quad (2)$$

wherein the weights are calculated as follows:

$$w_z = 0.5 \times (1 - w_{zx}), \quad (3)$$
$$w_l = w_{zx}(1 - w_x),$$
$$w_r = w_{zx} w_x,$$
$$w_x = \frac{x(s) - x(s-1)}{x(s+1) - x(s-1)},$$
$$w_{zx} = \frac{2h_{det}}{2h_{det} + x(s+1) - x(s-1)}.$$

The quantity $h_{det}$ is the detector height at the detector and the quantity $x(s)$ is the x-coordinate of the detector s at the detector spine. The detectors are equidistant only along columns (along the Z-axis) of the detector array $N_{row} \times N_{det}$. The detectors in the same row (along the X-axis) are not equidistant due to the curvature of the detector spine. At the boundaries the bilinear interpolation scheme is modified to use all the available nearest neighbors (two or three depending on the boundary). Specifically, $$P_{XZ}[v, s, r] = \begin{cases} w_z P[v, s, r+1] + w_l P[v, s-1, r] + \\ \quad w_r P[v, s+1, r], & r = 0 \text{ and } s \text{ is even} \\ (1-w_1) P[v, s, r+1] + w_1 P[v, s+1, r], & r = 0 \text{ and } s = 0 \\ (1-w_2) P[v, s, r+1] + w_2 P[v, s-1, r], & r = 0 \text{ and } s = N_{det} - 1 \\ w_z P[v, s, r+1] + w_l P[v, s-1, r] + \\ \quad w_r P[v, s+1, r], & r = N_{row} - 1 \text{ and } s \text{ is odd} \\ (1-w_1) P[v, s, r-1] + w_1 P[v, s+1, r], & r = N_{row} - 1 \text{ and } s = 1 \\ (1-w_2) P[v, s, r-1] + w_2 P[v, s-1, r], & r = N_{row} - 1 \text{ and } s = N_{det} - 2 \\ w_{z1} P[v, s, r+1] + w_{z1} P[v, s, r-1] + \\ \quad w_{r1} P[v, s+1, r], & r \text{ is even and } s = 0 \\ w_{z2} P[v, s, r+1] + w_{z2} P[v, s, r-1] + \\ \quad w_{l1} P[v, s-1, r], & r \text{ is odd and } s = N_{det} - 1 \end{cases} \quad (4)$$

wherein the weights are calculated as follows:

$$w_z = 1 - w_{zx}, \quad (5)$$

$$w_l = w_{zx}(1 - w_x),$$

$$w_r = w_{zx}w_x,$$

$$w_x = \frac{x(s) - x(s-1)}{x(s+1) - x(s-1)},$$

$$w_{zx} = \frac{h_{det}}{h_{det} + x(s+1) - x(s-1)},$$

$$w_1 = \frac{h_{det}}{h_{det} + x(s+1) - x(s)},$$

$$w_2 = \frac{h_{det}}{h_{det} + x(s) - x(s-1)},$$

$$w_{r1} = \frac{2h_{det}}{2h_{det} + x(s+1) - x(s)},$$

$$w_{z1} = 0.5 \times (1 - w_{r1}),$$

$$w_{l1} = \frac{2h_{det}}{2h_{det} + x(s) - x(s-1)},$$

$$w_{z2} = 0.5 \times (1 - w_{l1}).$$

Linear Interpolation along the X-axis

In the case of linear x interpolation, the removed detector samples are interpolated from neighboring samples in the same row using linear interpolation. If the missing sample is on either end of the detector spine, the missing value is replaced by the neighboring detector value. In particular, the removed detector samples are calculated as follows:

$$P_X[v, s, r] = \begin{cases} w_l P[v, s-1, r] + w_r P[v, s+1, r], & s+r \text{ is even} \\ P[v, 1, r], & s = 0 \text{ and } r \text{ is even} \\ P[v, N_{det} - 2, r], & s = N_{det} - 1 \text{ and } r \text{ is odd} \\ P[v, s, r], & \text{otherwise} \end{cases} \quad (6)$$

wherein the weights are computed as:

$$w_r = \frac{x(s) - x(s-1)}{x(s+1) - x(s-1)}, \quad (7)$$

$$w_l = 1 - w_r.$$

The quantity x(s) is the x-coordinate of the detector s at the detector spine. By design the detectors are not equidistant along the same row. We use the x-coordinate of each detector location x(s) to compute interpolation weights wr and wl.

In the case of Lagrange x interpolation, the removed detector samples are interpolated from neighboring samples in the same row using four point Lagrange interpolation. Specifically, the removed detector samples are computed as follows:

$$P_{Lag}[v, s, r] = \begin{cases} \sum_{k=-2}^{1} h(s, k) P[v, s + (2k+1), r], & s+r \text{ is even} \\ P[v, s, r], & \text{otherwise} \end{cases} \quad (8)$$

wherein h(s, k) are the Lagrange interpolation coefficients.

The Lagrange interpolation coefficients are calculated as follows:

$$h(s, k) = \frac{\prod_{j=-2}^{1} (x(s) - x(s + (2j+1)))}{\prod_{j=-2, j \neq k}^{1} (x(s + (2k+1)) - x(s + (2j+1)))}, \quad (9)$$

wherein the quantity x(s) is the x-coordinate of the detector s at the detector spine. The missing detector values are replaced by the neighboring detector values at the boundaries.

At the boundaries, the Lagrange interpolation scheme is modified as follows:

$$P_{Lag}[v, s, r] = \quad (10)$$

$$\begin{cases} \sum_{k=-1}^{2} h(s, k) P[v, s + (2k+1), r], & s = 2, r \text{ is even or } s = 1, r \text{ is odd} \\ \sum_{k=-3}^{0} h(s, k) P[v, s + (2k+1), r], & s = N_{det} - 1, r \text{ is even or } s = N_{det} - 2, r \text{ is odd} \\ P[v, s+1, r], & s = 0 \text{ and } r \text{ is even} \\ P[v, s-1, r], & s = N_{det} - 1 \text{ and } r \text{ is even} \end{cases}$$

The Lagrange interpolation coefficients h(s, k) are calculated by equation (9) with the modification of limits of the product as in equation (10).

The foregoing provides implementation schemes for easily upgrading existing single energy CT scanners, particularly of interest to security applications, to obtain dual energy imaging capability for reducing the false alarms from the automatic threat detection system. The implementations decrease the costs of CT security scanners while maintaining many of the advantages of dual energy CT scanning systems in a simple and easy way to convert current single energy scanners into dual energy scanners. As described, the implementation scheme uses a filter mask with a pattern of two or more sections, such as a checker board layout, placed on top of a two-dimensional detector array to provide a dual energy implementation. Such a dual energy implementation scheme does not require a design change of the existing beam-line of a single energy CT scanner to be upgraded into a dual energy CT scanner. The material and the thickness of the filter mask are chosen to maximize the x-ray spectral separation between the high-energy and low-energy spectra while a) maintaining the dynamic ranges of the X-ray photons within the limits of the detectors and corresponding electronics; and b) offering enough penetration for objects to be scanned. The spectral separation can be defined by a weighted sum of the high-energy and low-energy projection differences of a collection of objects of interest, and can be simulated using scanner geometry, X-ray source, and detector properties to perform the optimization over materials and thicknesses of a material. Any one of several interpolation schemes can be used to generate both high-energy and low-energy projection data of the complete detector array. The interpolation step can be incorporated into the cone-beam to fan-beam conversion, for example, NSR (Nutating Slice Reconstruction) interpolation. A flying focal spot technique can be used to compensate for the reduction of the image resolution.

What is claimed is:

1. A CT scanner comprising:
   at least one source of X-rays within an x-ray spectra;
   a detector array comprising a plurality of detectors; and
   an X-ray filter mask arrangement disposed between the at least one source of X-rays and detector array so as to modify the spectra of the X-rays transmitted from the at least one source through the filter mask arrangement to at least some of the detectors so that the X-ray spectra detected by at least one set of detectors is different from the X-ray spectra detected by at least one other set of detectors;
   wherein the CT scanner has X, Y and Z-axes, wherein the X and Y-axes define a scanning plane, and the Z-axis defines the axis of rotation of the at least one source of X-rays and detector array, and the CT scanner further comprises a processor arrangement configured so as to process signals from the detectors to generate interpolated data so that the set of interpolated data representing interpolated values is provided in accordance with a four point Lagrange interpolation along the X-axis.

2. A CT scanner according to claim 1, wherein the at least one source of X-rays is a source providing x-rays of a first energy spectra, and the filter mask arrangement provides x-rays of a second and different energy spectra so that some of the detectors receive x-rays of the first energy spectra and some of the other detectors receive x-rays of the second energy spectra such that use of the filter mask arrangement converts a single energy scanner into a dual energy scanner.

3. A CT scanner according to claim 1, wherein the at least one source of X-rays is a source providing a first set of x-ray energy spectra, and the filter mask arrangement provides x-rays of a second and different set of x-ray energy spectra so that some of the detectors receive x-rays of the first set of energy spectra, and some of the other detectors receive x-rays of the second set of energy spectra such that use of the filter mask arrangement increases the number of projections associated with different x-ray energy spectra.

4. A CT scanner according to claim 1, wherein the at least one source of X-ray includes an x-ray tube with a flying focal spot.

5. A CT scanner according to claim 1, wherein the X-ray filter mask arrangement is disposed between scanning objects and the detector array.

6. A CT scanner according to claim 1, wherein the X-ray filter mask arrangement is disposed between scanning objects and the at least one source of X-rays.

7. A CT scanner according to claim 1, wherein the X-ray filter mask arrangement includes a checker board pattern.

8. A CT scanner according to claim 1, wherein the CT scanner further includes a processor arrangement configured so as to interpolate data received by the detectors corresponding to one X-ray spectrum to generate the data corresponding to the remaining detectors that correspond to other X-ray spectra and apply an image reconstruction algorithm using the interpolated data for reconstruction.

9. A CT scanner according to claim 8, wherein the CT scanner has an X, Y and Z-axes, wherein the X and Y-axes define a scanning plane, and the Z-axis defines the axis of rotation of the at least one source of X-rays and detector array, and the CT scanner further comprises a processor arrangement configured so as to process signals from the detectors to generate interpolated data so that the set of interpolated data representing interpolated values is provided in accordance with an interpolation technique along the Z-axis.

10. A CT scanner according to claim 8, wherein the CT scanner has an X, Y and Z-axes, wherein the X and Y-axes define a scanning plane, and the Z-axis defines the axis of rotation of the at least one source of X-rays and detector array, and the CT scanner further comprises a processor arrangement configured so as to process signals from the detectors to generate interpolated data so that the set of interpolated data representing interpolated values is provided in accordance with a four point Lagrange interpolation along the X-axis.

11. A CT scanner according to claim 1, wherein the CT scanner further includes a processor arrangement configured so as to apply a reconstruction algorithm with steps modified to reconstruct data received by the detectors corresponding to one X-ray spectrum.

12. A CT scanner according to claim 11, wherein the reconstruction algorithm is a nutated slice reconstruction algorithm.

* * * * *